United States Patent
Dijkstra et al.

(10) Patent No.: US 10,874,086 B2
(45) Date of Patent: Dec. 29, 2020

(54) ROBOTIC INJECTION SYSTEM FOR DOMESTIC HERD ANIMALS

(71) Applicants: Marinus Dijkstra, San Jacinto, CA (US); Alexander Mika'ele Chuck, Norco, CA (US)

(72) Inventors: Marinus Dijkstra, San Jacinto, CA (US); Alexander Mika'ele Chuck, Norco, CA (US)

(*) Notice: Subject to any disclaimer, the term of this patent is extended or adjusted under 35 U.S.C. 154(b) by 366 days.

(21) Appl. No.: 16/027,015

(22) Filed: Jul. 3, 2018

(65) Prior Publication Data
US 2019/0008117 A1 Jan. 10, 2019

Related U.S. Application Data

(60) Provisional application No. 62/528,762, filed on Jul. 5, 2017.

(51) Int. Cl.
| | |
|---|---|
| A01K 13/00 | (2006.01) |
| A61D 7/00 | (2006.01) |
| A01K 7/02 | (2006.01) |
| A61B 34/32 | (2016.01) |
| B25J 9/16 | (2006.01) |
| A01K 5/02 | (2006.01) |
| A61B 34/30 | (2016.01) |

(Continued)

(52) U.S. Cl.
CPC .............. *A01K 7/02* (2013.01); *A01K 5/02* (2013.01); *A01K 13/003* (2013.01); *A61B 34/30* (2016.02); *A61B 34/32* (2016.02); *A61D 7/00* (2013.01); *B25J 9/1684* (2013.01); *A01K 11/006* (2013.01); *A01K 29/005* (2013.01); *A61B 2034/305* (2016.02)

(58) Field of Classification Search
CPC ................................ A01K 13/003; A61D 7/00
USPC ......................................... 119/518, 650, 652
See application file for complete search history.

(56) References Cited

U.S. PATENT DOCUMENTS

| | | | |
|---|---|---|---|
| 6,688,255 B2* | 2/2004 | Donaldson | A01K 67/033 |
| | | | 119/6.5 |
| 6,938,576 B2* | 9/2005 | van der Lely | A01K 1/12 |
| | | | 119/14.02 |

(Continued)

FOREIGN PATENT DOCUMENTS

WO 2016210135 A1 12/2016

*Primary Examiner* — David J Parsley
(74) *Attorney, Agent, or Firm* — Kenneth Avila

(57) ABSTRACT

A robotic injection system is herein described for delivering vaccines, reproductive hormones, and liquid materials to domestic herd animals. The robotic injection system includes a cooling-unit for storage of the liquid materials to be injected, a series of automatic gates to control the movement of herd animals, an RFID and camera ID reading system utilized for tracking identification numbers and medical history, a robotic arm to position and apply force in the injection process, and an injection mechanism for delivering injections to the patient. A streamlined system is described in delivering necessary injections to a mass number of domestic herd animals. A robotic injection system for injecting an accurate dosage of more than one fluid is described. For this description, bovines will be used as the primary example but this described invention also applies to other domestic herd animals such as sus, equus caballus, ovis aries, and capra aegagrus hircus.

15 Claims, 10 Drawing Sheets

(51) Int. Cl.
*A01K 29/00* (2006.01)
*A01K 11/00* (2006.01)

(56) References Cited

U.S. PATENT DOCUMENTS

| | | | |
|---|---|---|---|
| 7,922,688 | B2 | 4/2011 | Bodduluri et al. |
| 9,364,171 | B2 | 6/2016 | Harris et al. |
| 9,510,783 | B2 | 12/2016 | Hadjioannou et al. |
| 9,550,029 | B2 | 1/2017 | Boyden et al. |
| 2014/0140582 | A1* | 5/2014 | Spicola, Jr. ............... G06T 7/70 |
| | | | 382/110 |
| 2015/0100037 | A1* | 4/2015 | Allsup ................ A01K 13/002 |
| | | | 604/503 |

* cited by examiner

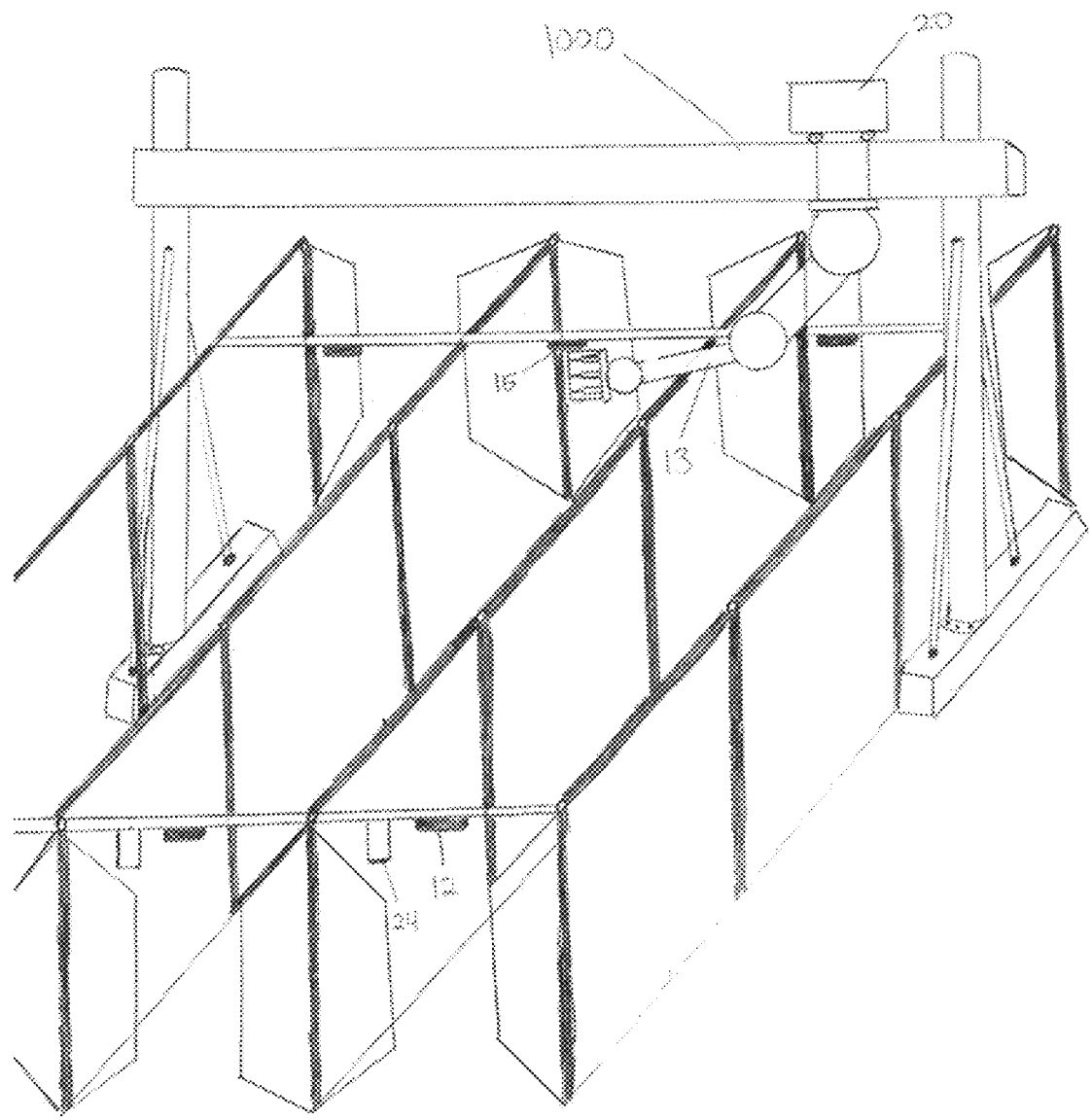

ROBOTIC INJECTION SYSTEM FOR DOMESTIC HERD ANIMALS

CROSS-REFERENCE TO RELATED APPLICATIONS

This application claims priority from U.S. Provisional Patent Application No. 62/528,762 filed on Jul. 5, 2017. The entire disclosure of the prior application considered to be part of the disclosure of the accompanying application and is hereby incorporated by reference.

BACKGROUND OF THE INVENTION

This invention relates to an apparatus for the subcutaneous or intramuscular injection of liquid materials. This apparatus serves for delivering automatic injections to bovines, sus, equus caballus, ovis aries, and capra aegagrus hircus and more particularly, serves as an improvement to an apparatus, capable of self-positioning a robotic arm with the assistance of a two dimensional (2D) and an attached thermal camera. The combination of these systems facilitates a feasible way to identify the desired location on any of these animals to inject reproductive hormones, vaccines, liquid medication, and any other liquid material that a farmer may deem necessary to inject. For the sake of describing this invention, we will use bovines as the patients receiving the injections. Using bovines in describing this invention also creates more clarity for the system being described in detail.

Prior art of this invention falls into three broad categories. These categories include subcutaneous dispensers, jet injectors, and subcutaneous fluid dispensers. In accordance with the invention, a robotic arm, positioning and controlling an injection mechanism is employed to inject liquid material into a selected region of tissue on a bovine, for example, this tissue region would be selected for to have reproductive hormones injected into the bovine's hide measuring between 4 mm and 8 mm of thickness.

In the injection process with bovines, injections must be given by an employee in a timely manner and must be accurate when injecting. With manual injection systems and extended shot arms being currently available, there is a realization of unnecessary costs of labor and errors from human use when injections are delivered like they currently are.

The cost of labor would specifically include the cost for an employee to deliver injections to the bovine, as well as taking time out of the work day to ensure injections are organized and liquid material is constantly refilled when materials are depleted. An employee would be replaced with robotic technology. With costs to actively manage an employee to provide shots to a bovine, the robotic arm would pay itself off within the first couple years of use. After those first couple of years, the cost of purchasing the equipment required for this apparatus would disappear and the firm would strive off the self-sufficiency the mechanism contains.

This technology would be capable of self-positioning itself in the suggested area for injection. With the assistance of a 2D guidance system and a thermal camera attached to the robotic arm, the arm can adjust if need be, for a more accurate point of injection. The thermal camera can highlight the area and coordinate through laser technology the most ideal area for injection before proceeding with subcutaneous or intramuscular injections to the bovine. The injection mechanism has a pressure gauge on the robotic mechanism to ensure the animal isn't harmed in the injection process.

The only point in time an employee would need to intervene with the improved invention is either when the robotic arm runs out of medication it is injecting, the refrigerator storing the suggested medication next to the robotic arm malfunctions, or in the case of adjusting the thermal camera for a newly targeted region of tissue. There would be no need to have constant over watch with the robotic injection system. The cooling unit that stores the suggested medication, is located next to the robotic arm on the outside of the exit lane. These cooling units can hold various sizes of containers of liquid material. The different containers of liquid material depend on what the veterinarian prescribed as well as how many containers the acting dairy manager stocks for that specific session of injections. When the liquid material is depleted, the dairy manager or lead herdsman for the facility will be notified via mobile application and will then initiate the dairy manager or lead herdsman to refill the suggested containers of liquid material.

Human errors could occur with injections if an employee adds too much or too little of a dosage for the ideal intake suggested for the bovine, in the case of manual injections. Bovines have information provided by the veterinarian of the facility and a dairy management computer program which both assists and decides the suggested doses of liquid material to maintain healthy lives. These injections include vaccines, reproductive hormones, and/or liquid medication in general suggested for use to the bovine. Employees are provided with this information as well as the related amounts each bovine needs for their suggested dose. If employees manually inject the bovine with the wrong liquid material, the bovine's daily life and health could change accordingly and could potentially affect the bovine in a negative manner.

In the case of manual injections, a needle injected into a bovine can be misplaced by an employee and could be delivered to a spot that is less ideal than the area suggested by pharmaceutical standards. Employees injecting bovines with liquid material are provided with information regarding the area to properly inject the bovine. If an experienced or inexperienced employee manually puts the needle in the incorrect area, the bovine will not receive as of an effective dosage as it could of if it were self-automated. Other problems could occur with an employee using needles manually such as the risk of a needle breaking in a bovine, using a needle that is unsanitized, or using equipment in general that is not properly sanitized. The risks stated above could put the bovine at risk for receiving an infection and ultimately causing the animal harm.

Bovines could as well be potentially misidentified by employees and the wrong liquid material could be given to the wrong bovine. Another conflict in delivering manual injections to bovines is giving injections to bovines that do not need liquid materials to be injected. Bovines are given identification tags located on their ears at most dairies. The numbers on the identification tag could appear very similar from one another to employees of the facility. The employees could then give a shot to a bovine who they think is the correct bovine for the designated liquid material when in fact the correct bovine is in a completely different pen on the facility. Radio Frequency Identifiers (RFIDs) and a camera identifier (ID) reader positioned at the site of the robotic injection system would remove this conflict.

The accomplishment with this improvement to the current invention is to provide a streamlined and accurate apparatus, capable of making self-automated injections and inducing liquid materials to bovines where there is no room for error. With this accomplishment, a system for delivering self-automated injections will be created; the cost of labor and management will be cut out of that specific portion of the facility; a system will be facilitated for providing accurate dosages; errors will be eradicated; and an automated system having sufficient identification abilities will be in place for the facility.

Secondary results that will occur due to the accomplishment of this improvement to the current invention includes causing less stress to the bovines; increasing milk production from bovines not being locked up in stanchions; more accurate injections given could lead to higher conception rates; providing a healthier herd from more accurate vaccines; a lower rate in cull bovines; and ultimately a lower death rate and better herd management.

Definitions

Bovines: We shall refer to the term "Bovines" to define a fully grown female animal of a domesticated breed of ox, used as a source of milk or beef. For this document, the word "bovine" shall represent an application for sus, equus caballus, ovis aries, and capra aegagrus hircus.

Subcutaneous (SubQ): We shall refer to the term "Subcutaneous" to define as being, living, occurring, or administered under the skin.

Intramuscular (IM): We shall refer to the term "Intramuscular" to define being situated in, occurring in, or administered by entering a muscle.

SUMMARY OF THE INVENTION

In accordance with this invention, an injection device will be employed, such as a SubQ or IM injection needles. This injection mechanism will be responsible for delivering a predetermined amount of liquid material to a coordinated region of tissue chosen on the bovine to inject. The SubQ or IM needle used to inject the bovine can penetrate between 4 mm and 8 mm of thickness of the bovine's hide. The dosage of liquid materials is predetermined and set by the acting manager of the dairy and under instruction from the dairy's veterinarian.

This robotic injection system is manipulated by a robotic arm with attached needles for SubQ or IM injections. The robotic arm is controlled by a dairy management computer program capable of communicating with RFIDs and the deployed camera identification reader. The robotic injection system may be applied to an operation with a herringbone, parallel, or rotary parlor depending on the preferred embodiment of the invention. As bovines move through exit lanes leaving the herringbone or parallel milking parlor, they approach the site of the operation where they will receive the injections. A RFID will be located at the same site as the injection site. The camera ID reader recognizes the identification number of the bovine approaching the injection site. Collaborating with the first RFID in the injection site, it will be determined whether or not a bovine will require an injection. These identification sensors transmit information to the computer responsible for manipulating the robotic arm. As bovines enter this site, an automatic gate closes behind the bovine that is about to receive the robotic injection, assuming the bovine requires an injection. The robotic arm loads the suggested material for that specific bovine by allowing pressure to dispense a predetermined dosage into the syringe or syringes as well as selecting a different sanitized needle after every 50 bovines that receive injections. Before the needle injects liquid material, an infrared camera and 2D guidance system locates the coordinates of the ideal injection site on the bovine. These two systems also collaborate with laser technologies within one of the cameras attached to the robotic arm to locate an ideal spot to deliver the injection. There may also be an optional application involving the injection mechanism delivering needleless SubQ or IM injections to bovines. These air-injections could be achieved through high amounts of pressure and velocity being derived within a component of the injection mechanism.

Vaccines, reproductive hormones, or any type of liquid material may be used in a minimum of 1 syringe and a maximum of 10 syringes on the injection mechanism with any combination of allocated liquid materials depending on the preferred embodiment of the invention. Liquid material is distributed through tubes connecting the cooling unit to the injection mechanism. For example, if 6 syringes are in use on the injection mechanism, there will be 6 tubes connected to the cooling unit allowing for the flow of reproductive hormones or vaccines. 3 of the tubes may be used for reproductive hormones and 3 may be used for vaccines. Another example could include 6 tubes but this time 4 are allocated for reproductive hormones and 2 for vaccines. This all varies on the preferred embodiment of the invention. In addition, the tubes will be enclosed by a refrigerated line to regulate the temperature of the liquid materials within the tubes. The flow of liquid materials will be controlled by a traditional plunger or instead may utilize a peristaltic pump located on the injection mechanism. If the injection mechanism requires 5 cc of liquid materials the traditional plunger or peristaltic pump will only allow for 5 cc flow of liquid materials. The remaining liquids shall remain in the refrigerated tubes until the traditional plunger or optional peristaltic pump allows movement and liquids will also remain within bottles located in the cooling-unit. For this presented invention, there will be traditional plungers used rather than rotary-style chemical pumps or peristaltic pumps.

Depending on the preferred embodiment of the invention a spray paint add-on, teat dipping add-on, or sanitation spray add-on may be applied to the robotic arm in addition to the injection mechanism. The spray paint add-on can mark cows with different colored paints for heat detection purposes. For example, after a cow receives a shot, the robotic arm shall position itself towards the rear-end or head of the bovine. Here the injection mechanism shall spray a specified color of paint derived from a cartridge of spray paint located on the injection mechanism itself. The teat spraying add-on would be applied on rotary-styled milking parlors. For example, after a bovine receives an injection, a cartridge loaded with a cleaning solution such as iodine would be applied to the bovine's teats. This would occur by the robotic arm positioning itself underneath the rear-end of the bovine. The sanitation spray add-on can sanitize the needles on the injection mechanism after every delivered shot. For example, after a bovine receives a shot, sanitizer would be sprayed from a cartridge on the injection mechanism or there may be an application utilized where the robotic arm dips the injection mechanism in a solution in between every injection. The applications presented above shall not be used in this presented invention as these add-ons are optional.

Accompanying this robotic injection system exists an infrared camera. This infrared camera allows access to visibility of the animal's optimal target region for injection of liquid material. The infrared camera will be programed to work with the robotic arm and facilitate ideal coordinates for injection based off a 2D guidance system and laser technology programmed within the robotic arm. The infrared camera will also consider which bovine it is analyzing. The infrared camera will receive this information through the first RFID, camera ID reader, and second RFID placed at the actual site where injections will take place.

This 2D guidance system programmed within the robotic arm allows anatomical area of a bovine's body as defined by location coordinates locating the select body area with respect to a structure supporting the bovine in collaboration with the laser technology. This combined 2D guidance system can move the robotic arm accurately to the desired spot for injection on the bovine. The guidance system will have further accuracy with the assistance from the coordinates formed on the infrared camera and through laser technology. With the 2D guidance system's adaptability feature programmed in the robotic arm, an ideal location can be easily adjusted for different bovines entering the injection site if need be. A separate computer to control the robotic arm will not be needed at the facility because the thermal camera, 2D and guidance system are integrated within the robotic injection system.

At the site where injections are delivered, two automatic gates will exist. These automatic gates allow for the entry of one bovine at a time to receive injections, assuming the bovine requires an injection. The automated gates will be instructed to remain open upon scanning a bovine with the first of two RFIDs if the bovine does not require an injection. This first RFID is located 10 feet, give or take, from the robotic arm. These automatic gates will only close if a bovine is scanned by the first RFID and camera ID reader and the bovine requires an injection. There will then be enough time for the bovine to enter the injection site before closing and restricting access to the succeeding bovine. Depending on the preferred embodiment of the invention, a QR Code or traditional bar code may be placed on the ear tag for identification purposes. For the sake of this presented application, QR codes and traditional bar codes shall not be used on the ear tag for identification purposes.

RFIDs will be located at two different areas of the injection site. The first RFID will be located 10 feet or so, before the robotic arm. Here there will also be a camera ID reader. This first RFID allows for identification of the bovine that is about to have injections delivered to them, scanning whether or not the bovine requires one at that specific point in time. The automatic gate will remain open to allow for the bovine to enter the injection site, assuming the bovine requires an injection. After this first RFID and camera ID reader scans the bovine for identification purposes, the automatic gate will close behind the bovine that approached the injection area where it will be scanned by the second RFID. The second RFID serves as a recognition tool and will analyze bovines that entered the injection site. Once bovines are scanned by this second RFID scanner, information pertaining to medical records will be transmitted to the robotic injection system. Prior to receiving a shot from the injection mechanism, the bovine shall be pushed towards the robotic arm and injection mechanism by a bumper serving as a restraint allowing for limited movement when the shot is delivered. For this presented invention, the bumper add-on in the injection area will not be used as it is an optional function to have. Depending on the preferred embodiment of the invention, a facial recognition camera with an ear tag reader or QR code reader may be utilized as an additional way to identify bovines in this process. For the sake of the presented invention, these applications shall not be applied as they are optional to have on the system. Once the robotic injection system receives the information derived from the dairy management computer program, appropriate doses of the required medication will be passed from the cooling-unit outside of the exit lane to the robotic arm that holds the needle for injection through refrigerated lines. After the injection has been given to the bovine, information pertaining to the shot given, time, date, and which bovine it was given to will be transmitted to the acting herdsman or dairy management computer program in real time. By having information transmitted in real time, the dairy manager will have a better management program in this section of the facility's operations.

Furthermore, the information derived from the dairy management computer program utilizes a cloud-based system for storage of this information and is recorded in real-time using blockchain technologies. A cloud-based system used for storage is a cloud computing model in which data is stored on remote servers accessed from the internet, or "cloud." It is maintained, operated and managed by a cloud storage service provider on storage servers that are built on virtualization techniques. The data stored on this cloud-based system would be the bovine's medical records. Once a bovine receives a shot, the information provided to the dairy management computer program will record this information permanently on the blockchain. Blockchain technology creates an indelible record that cannot be changed; furthermore, the record's authenticity can be verified by the entire community using the blockchain instead of a single centralized authority. For the presentation of this current invention, cloud-based systems and blockchain technologies shall not be used as these are optional functionalities.

Predetermined doses will be selected for use by the acting herdsmen or manager of the dairy. The source of the liquid material is found in a cooling-unit located right outside of the exit lane. This cooling-unit is placed next to the exit lane and at the site where injections are administered. This cooling-unit may be equipped with a QR code reader or traditional bar code reader for scanning and identifying bottles stored within the cooling-unit. For the sake of the presented invention, there will not be a QR code or traditional bar code reader utilized within the cooling-unit as these are optional add-ons. Depending on recommended prescriptions from the veterinarian, ranging from 10 cc containers to 250 cc containers, will determine the number of containers stored in the cooling-unit. The cooling-unit could hold a range of 1-6 containers filled with liquid material for the predetermined doses. After a container of liquid material is chosen for one of the three injection mechanism's syringes, a sanitized needle will be utilized as well.

Each container is monitored by a sensor on the cooling-unit for when liquid material is less than 10%, if weight of liquid material doesn't show a change, or if a leak were to occur. The sensor is set off when the liquid material reaches one of these thresholds. This sensor is linked to a mobile application and dairy management computer program that sends a signal to the acting herdsman or manager of the dairy. In this case, the signal is transmitted through a text message on the mobile application. The text message transmitted to the acting herdsman or manager of the dairy contains the information of how much liquid material is left, along with which bottle needs to be refilled with a predetermined dose. The text message transmits the quantity as a percentage of depletion, sends a notification if there is no weight change in liquid material, or notifies the acting herdsman of dairy manager that a leak has occurred. If there is no response to the text message within one minute of the message being sent a follow-up message will be sent as well as a separate text being sent to the employee who is 2nd in command of the operation. The specific name for the dosage that needs to be refilled will be provided in the text message as well. After injections to the bovine have taken place, an automatic gate in front of the injection site will open to allow for the bovine to then proceed down the exit lanes of the facility.

Depending on the preferred embodiment of the invention, the robotic injection system may be utilized in a rotary-styled milking parlor. In a rotary-styled milking parlor the bovine stands on a circular raised platform. The platform rotates very slowly, allowing bovines to enter and exit the platform at regular intervals and enter individual stalls. The ideal place to set the robotic injection system on the facility would be near the exit of the circular raised platform. In addition, the cooling-unit would be placed in this area as well. The first RFID and Camera ID reader would be placed on the raised platform itself at least 20 ft after the entry lane of the rotary. The second RFID would be placed at least 20 ft before the bovine receives the injection. The injection system would then position itself to deliver an injection to the respective bovine. Before the injection is delivered, the injection mechanism must first recognize a bovine triggering the sensor in order for the injection to be received by the bovine. There wouldn't be a need to have sorting gates installed since the bovine would receive the injection before exiting the circular raised platform.

Therefore, a primary objective of the innovation to the present invention is to provide a system and methodology for accurately delivering liquid materials to a bovine at a coordinated anatomical position. It is a further objective to provide an automatic method and system that selects a suggested region for place of injection and is collaborated between the infrared camera and the 2D guidance system in the robotic arm. Other objects, features, and advantages of the improvements to the current invention will be evident in the light of the following detailed description with the referenced drawings of a preferred exemplary embodiment. Furthermore, this entire system is capable of being powered by solar panels and battery packs or traditional utilities and could also utilize the method of delivering air-injections, but for this presented invention, power for the equipment shall be derived from traditional utilities and injections shall be delivered through needles as the presented items are optional.

BRIEF DESCRIPTION OF THE DRAWINGS

FIG. 10 shows a detailed demonstration of how a rail system may be utilized to service multiple lanes for larger operations.

DETAILED DESCRIPTION OF THE INVENTION

Figure 1:
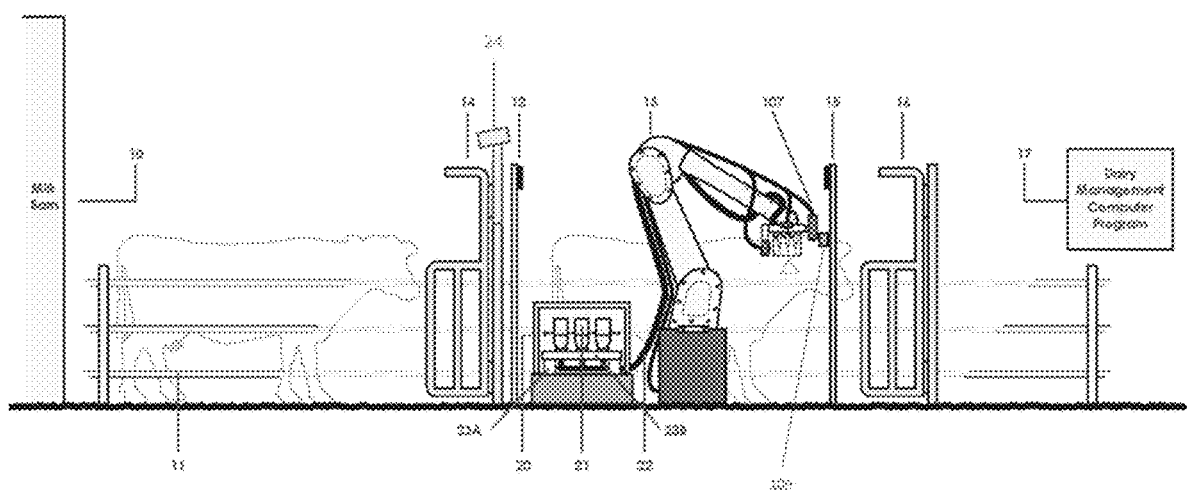
FIG. 1 is a schematic design and layout demonstrating bovine exiting a parallel or herringbone milking parlor whom then proceed to the robotic injection system in accordance with the present invention. This figure also shows the cooling unit containing the vaccines, reproductive hormones, and liquid medication prescribed by the dairy veterinarian, which all sit on a scale inside of the cooling unit to the allow liquid to flow from the cooling unit to the syringes on the head of the robotic arm.

In FIG. 1, bovines exit the milk barn 10 and proceed down an exit lane 11 towards the robotic injection system 13. This exit lane 11 leads bovines in a straight path to the robotic injection system 13. The first RFID 12 and camera ID reader 24 are located 10 or so feet away from the robotic arm 13. While the conventional use of RFIDs on bovines include monitoring the lifecycle, enabling individual yield improvement, disease control, and overall farm efficiency, this first RFID 12 and camera ID reader 24 in accordance to the present invention will close the first 14 and second 16 automated gates for the bovines, if they require an injection. More specifically, this first RFID 12 and camera ID reader 24 are responsible for scanning for two items which are the bovine's identification number and if the bovine requires an injection at that specific point in time. After a bovine is recognized by the first RFID 12 and camera ID reader 24 the first 14 and second 16 automated gates will close simultaneously if both the first RFID 12 and camera ID reader 24 validates this information, and in fact, that this specific bovine requires an injection according to its medical history. A second RFID 15 is located right next to the robotic injection system 13. The second RFID 15 scans bovines entering the injection site for their medical history and conception statistics to determine what type of injection will be delivered to the bovine. The information scanned by the second RFID 15 is transmitted to a dairy management computer program 17 and is updated in real time. The information transmitted will stay with the bovine and update in real time for the rest of the bovine's life. The first 14 and second 16 automated gates will open simultaneously once an injection has been delivered or will remain open for bovines who do not need injections delivered. In the case of a bovine not needing an injection, the bovine will be allowed continue through the exit lane, while only the automatic gate 14 near the first RFID 12 will close. An inside view of the cooling unit 20 which, therein, contains the necessary vaccines, reproductive hormones, and liquid material 21 is shown in this figure for the preferred embodiment of the invention. The vaccines, reproductive hormones, and liquid material 21 are divided into three sections respectively. These liquid materials 21 are divided respectively for feasible access when an employee is sent by the acting dairy manager to refill the depleted containers as well as creating an even distribution of liquid material 21 to flow through tubes 22 connecting to the robotic injection system 13. These liquid materials 21 sit with the necks of their respective containers popping out from the bottom of the cooling unit 20 and connect to plastic tubing 22 which ultimately connects to a syringe at the head of the robotic arm in the injection mechanism. The infrared camera 107, laser technology 109, and robotic injection system 13 will coordinate a selected tissue region on the bovine once liquid material 21 is loaded into the syringe, and will then proceed to deliver the injection. The vaccines, reproductive hormones, and liquid material 21 all sit on a scale 23a within the cooling-unit 20. This scale 23a measures how many cc's of liquid material is taken out of containers for each injection. The sensor 23b on the scale 23a updates the robotic injection system 13 and the dairy management computer program 17 in real time so liquid material 21 may be refilled or an issue may be addressed. The sensor 23b will alert the robotic injection system 13 and the dairy management computer program 17 if either liquid material 21 isn't flowing through the plastic tubing 22 that leads to the injection mechanism, liquid material 21 isn't changing in weight, liquid material 21 is changing weight too fast for the output of ccs, or if the container is empty and needs to be refilled. A text message will be sent once the robotic injection system 13 is notified if one of these events occurs. The text message sent to the acting dairy manager will provide a brief description on the situation that occurred, setting off the sensor 23b on the scale 23a. This text message will also provide action items the acting dairy manager will need to take to solve the situation and continue delivering injections to bovines.

Figure 2:
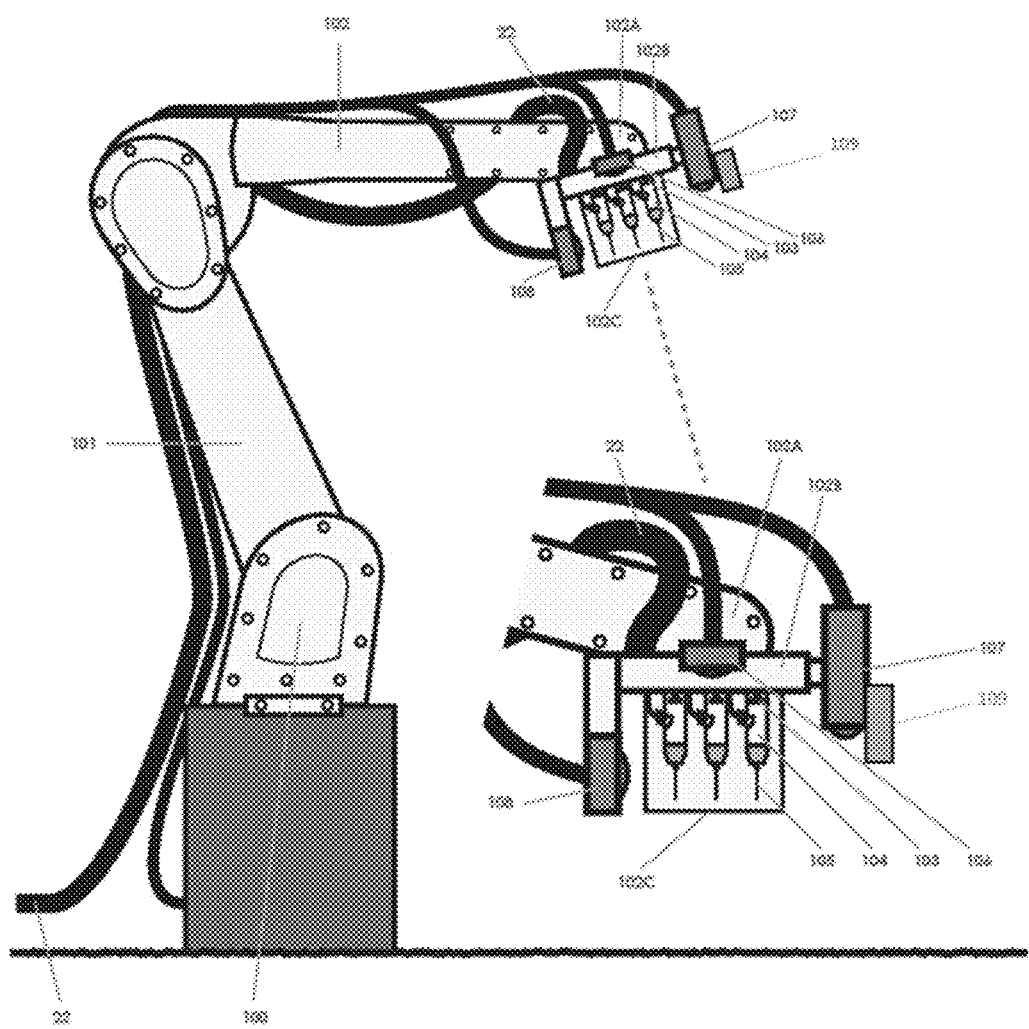
FIG. 2 shows a robotic arm, serving only as a positioning apparatus in the overall process of delivering vaccines, reproductive hormones, any liquid material the acting dairy manager may deem necessary for subcutaneous or intramuscular injections. This figure also shows the injection mechanism of the apparatus having one to three syringes containing the liquid material to be injected in the bovine.

FIG. 2 depicts the robotic arm 13 in accordance with the present invention. This robotic arm is a part of the improvement to the current invention and serves as a positioning mechanism in preparation for delivering automated injections. This robotic arm 13 is programmed to function on multiple axis', and therefore can position the injection needle 105 properly in accordance to the bovine's position. The base of the robotic arm 100 allows for left and right movements, allowing for the first 2 movement. The base 100 of this robotic arm serves a critical purpose in the case the arm needs to be slightly adjusted to accommodate the bovine's movement in the injection site. The next portion of the robotic arm is one of the necks 101 located on the arm. This first neck 101 on the robotic arm is responsible for moving the arm towards and away from the bovine during injections. When a bovine enters the site of injection and the RFID verifies the bovine needs an injection, this first neck 101 on the robotic arm will position itself close enough so the rest of the robotic arm can position itself close enough for the injection to be made. The next part of the robotic arm is the second neck 102, which is also responsible for adjusting and positioning itself for injections to be properly made to the bovine. This second neck 102 has a similar range of motion as the first neck 101. The second neck on the robotic arm is angled at a different, overhead position that has a better reach to initiate the injection. The head 102a of the robotic arm lies on a multi-twisting axis that allows the head 102a to move the injection mechanism at the end of the robotic arm. After the arm positions itself correctly in preparation for delivering injections, the head 102a of the robotic arm positions itself as well before delivering the injection. The 2D guidance camera 106, infrared camera 107, and laser technology unit 109 combine their technologies to create an ideal coordinated area on the bovine to deliver the injection. The head attached to the injection mechanism 102b then proceeds in delivering either SubQ or IM injections. The injection mechanism 102b has been attached to the head of the robotic arm 102a for the preferred embodiment of assembly to carry out this SubQ or IM injection method. This part of the injection mechanism 102b allows for vaccines, reproductive hormones, and liquid material used for SubQ or IM injections to flow through tubes 22 from the cooling unit to the injection mechanism 102b at the head of the robotic arm 102a. These tubes 22 are enclosed by refrigerated lines to ensure the fluid within doesn't overheat and spoil. A camera 108 is attached to the injection mechanism 102b to ensure the injection needle 105 is straight before proceeding with the injection. Depending on the SubQ or IM injection to be delivered to the bovine, either a veterinary prescribed vaccine, reproductive hormone, or some sort of liquid material will be loaded into one of three syringes 104 located on the injection mechanism 102b. The three syringes are labeled and use the respective medication depending on what will be delivered to the bovine for the SubQ or IM injection. At the base of syringe 104 is the plunger shaft 103 that locks the syringes 104 and injection mechanism 102b to the head of the robotic arm 102a. A flange 102c will surround the needle delivering injections. The needle 105 at the end of the injection mechanism 102b serves in delivering 50 SubQ or IM injections to bovines before the needle is ejected and a new needle 105 replaces it. The used needle 105 is replaced with needles loaded into a cartridge attached to the injection mechanism 102b. Once 50 or so bovines receive SubQ or IM injections, information will be transmitted to the robotic arm to eject the current needle 105 to an ejection cartridge and new needles 105 will be loaded into the injection mechanism 102b by the cartridge with the sanitized needles 105.

Figure 3:
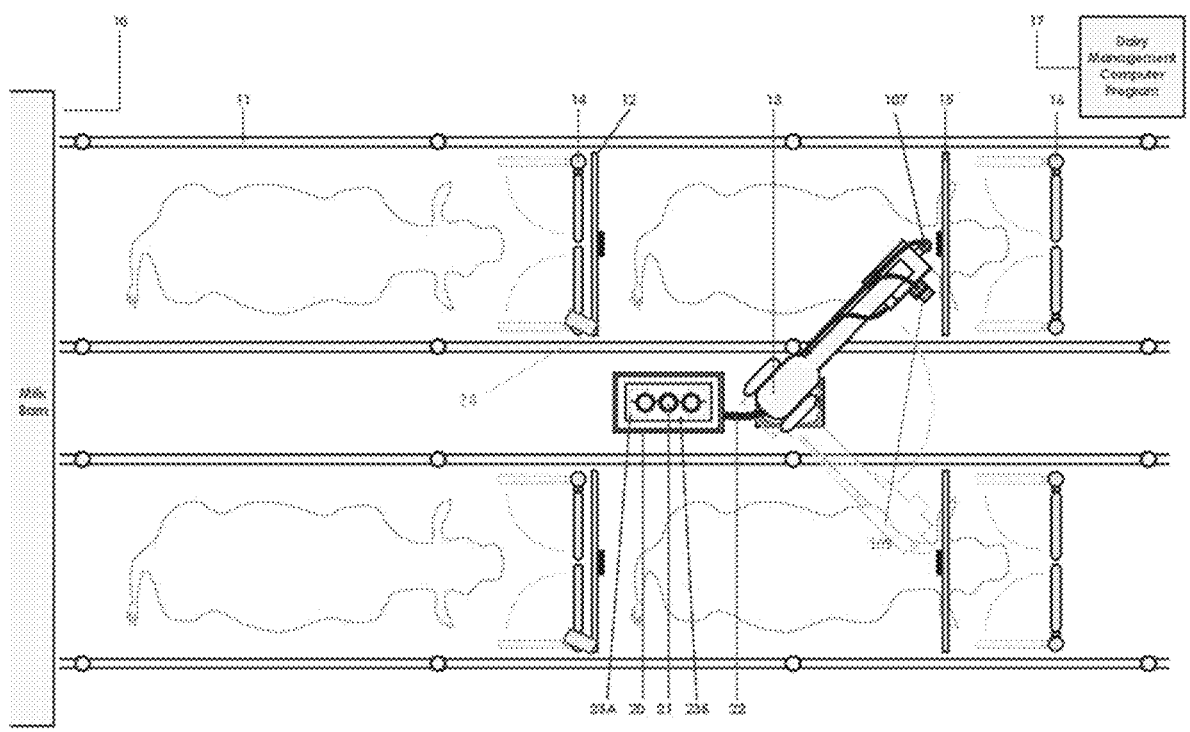
FIG. 3 is an overhead, schematic design and layout demonstrating both exit lanes utilizing the robotic injection system simultaneously as bovines move through each lane.

In FIG. 3, bovines exit the milk barn 10 through two exit lanes 11, splitting up the herd and leading towards the robotic injection system 13. One robotic injection system 13, infrared camera 107, and laser technology unit 109 will be responsible for coordinating ideal regions for delivering injections to bovines moving through two exit lanes and injection sites. The first set of RFIDs 12 in each lane are 10 or so feet away from the robotic injection system 13. The first set of RFIDs 12 and camera ID readers 24 in accordance to the present invention will open and close the automated gates 14, 16 for the bovines passing through. As previously stated, the first set of RFIDs 12 are responsible for scanning each passing bovine that approaches for identification purposes and after a bovine is recognized and validated by the first set of RFIDs 12 and camera ID readers 24 the first 14 and second 16 automated gate will remain open or close simultaneously depending on whether a bovine requires an injection. These automatic gates 14, 16 will open after an injection has taken place and will allow for enough time to elapse for the bovines to pass through before shutting and restricting access to the next set of bovines. The second set of RFIDs 15 are located right next to the robotic injection system 13. The second set of RFIDs 15 scan bovines entering the injection sites for their medical history and conception statistics to determine what type of shot the bovine needs at that point in time. The information scanned by the RFIDs 15 are transmitted to a dairy management computer program 17 and are updated in real time and in which the information transmitted will stay with the animal and update in real time for the rest of the animal's life. The second set of automatic gates 16 will open once either an injection has been delivered or will remain open for a bovine who does not need an injection to be delivered. In the case of a bovine not needing an injection, the bovines will be allowed continue through the exit coral. Only one cooling-unit 20, with liquid materials 21, a scale 23*a*, a sensor 23*b*, and plastic tubes 22 coming out from beneath the cooling-unit will be necessary for this preferred embodiment.

Figure 4:
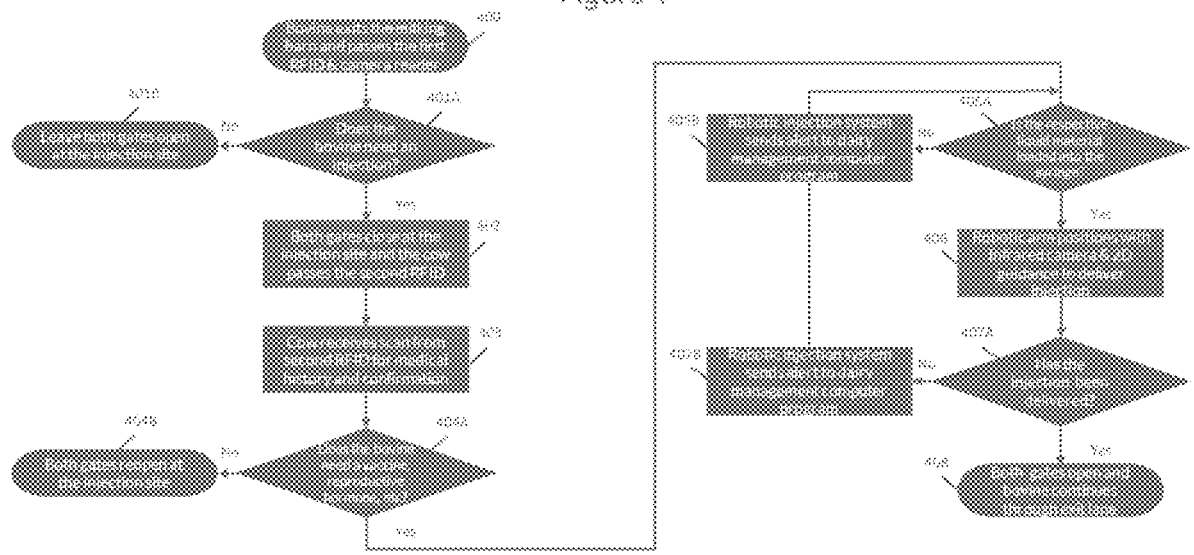
FIG. 4 is a flowchart outlining the injection process for bovines exiting the milking parlor.

In FIG. 4, the process begins with the bovine exiting the milking parlor and moving down the exit lanes. As the bovine moves through these exit lanes, it will approach the area of the operation where injections are delivered to bovines. The bovine then passes the first RFID and camera ID reader that will scan the bovine's identification tag 400. The camera ID reader will simultaneously scan the bovine's ear tag and facial features to confirm that the correct bovine is about to potentially receive an injection. The question then arises, does the bovine require an injection 401A? If the bovine does not require an injection at that point in time both gates located near the robotic injection system shall remain open 401B. If the bovine requires an injection, both automated gates located near the robotic injection system shall close and the bovine will pass a second RFID 402. The second RFID will then scan the bovine for medical history 403 to determine which shot will be injected into the bovine at that point in time according to either it's immunization protocol or artificial insemination program. Furthermore, the question would then arise, does the bovine need a vaccine or reproductive hormone 404A? Base off the information derived from the dairy management computer program, the bovine will receive an injection of one of the options. If the bovine in fact was scanned incorrectly by the first RFID and camera ID reader, the second RFID notifies the dairy management computer program and the automated gates located near the robotic injection system shall reopen 404B and allow for the bovine to move down the exit lane back to its respective corral. If the bovine does indeed require an injection based off of its medical history, then another question shall arise; is the respective liquid material loaded into the syringe 405A within the injection mechanism? If the respect liquid material is not loaded into the syringe, the robotic injection system will send an alert in real-time to the dairy management computer program 405B and will also send a text message through via mobile application to the on-site dairy manager. If the respective liquid material is loaded into the syringe on the injection mechanism then the robotic arm will then position itself with an infrared camera, 2D guidance system and laser technology 406 to calculate an algorithm that will produce an ideal location on the neck of the bovine. After the robotic arm positions itself and delivers the injection to the bovine there will be a question that then arises. Has the injection actually been delivered to the bovine 407A? This information shall be derived from the sensor located at the end of the injection mechanism as well as the depletion of liquids in the syringe and cooling unit. If the injection wasn't delivered, the robotic injection system will send an alert in real-time to the dairy management computer program 407B and will also send a text message to the on-site dairy manager. If this step occurs, then the process will go back to asking the question, is the respective liquid material loaded into the syringe 405A? The process will not proceed until the robotic injection system has been corrected or validated by on-site management. Once the system has been corrected and the injection has been delivered to the bovine, then both automated gates located near the robotic injection system shall open 408 and allow the bovine to continue through the exit lanes leading to its respective corral.

Figure 5:
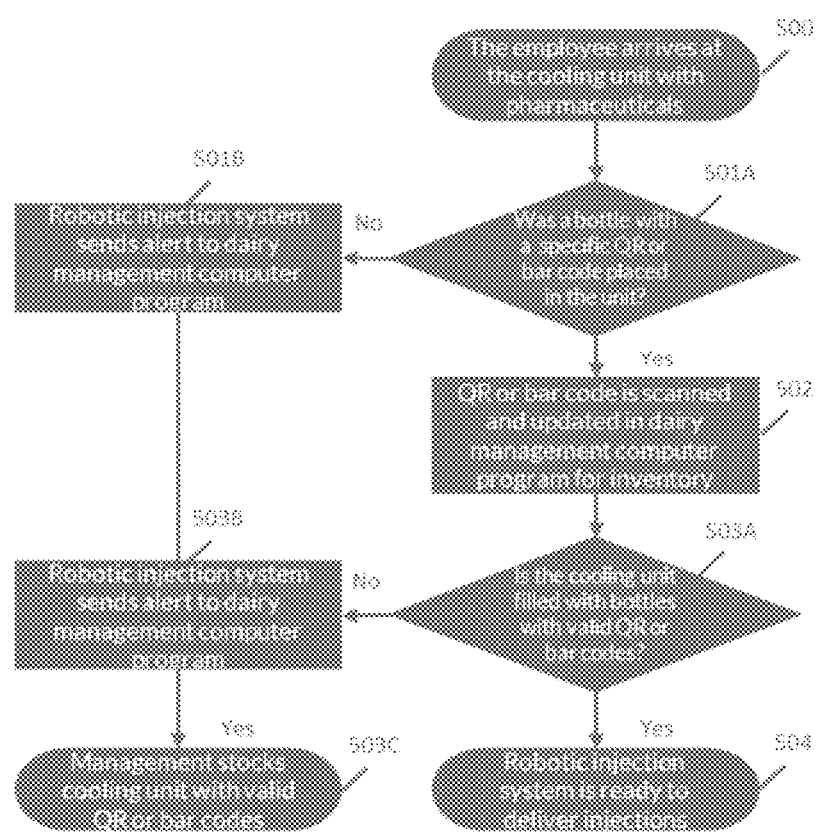
FIG. 5 is a flowchart outlining the process for adding inventory to the cooling unit that stores pharmaceuticals for the robotic injection system.

In FIG. 5, the process begins with an employee or vendor arriving at the cooling unit 500 with a new batch of pharmaceuticals for the cooling unit's inventory. The first question then arises, was a bottle with a specific QR or bar code place within the cooling unit 501A? If not, the robotic injection system will send an alert in real-time to the dairy management computer program 501B and will also send a text message to the on-site dairy manager. After this occurs management will be requested to check on the cooling unit and validate the bottles placed within the cooling unit 503C. If bottles with specific QR or bar codes are placed within the cooling unit 501A then the specific QR or bar code will be scanned and updated in the dairy management program to show bottles are being loaded into the cooling unit and to account for inventory 502. The question then arises, is the cooling unit filled with bottles with valid QR or bar codes 503A? If not, the robotic injection system will send an alert in real-time to the dairy management computer program 503B and will also send a text message to the on-site dairy manager. After this occurs management will be requested to check on the cooling unit and validate the bottles placed within the cooling unit 503C. If the cooling unit is validated through the system and is fully stocked with inventory, then the process will end with the robotic injection system prepping to deliver injections to bovines 504.

Figure 6:
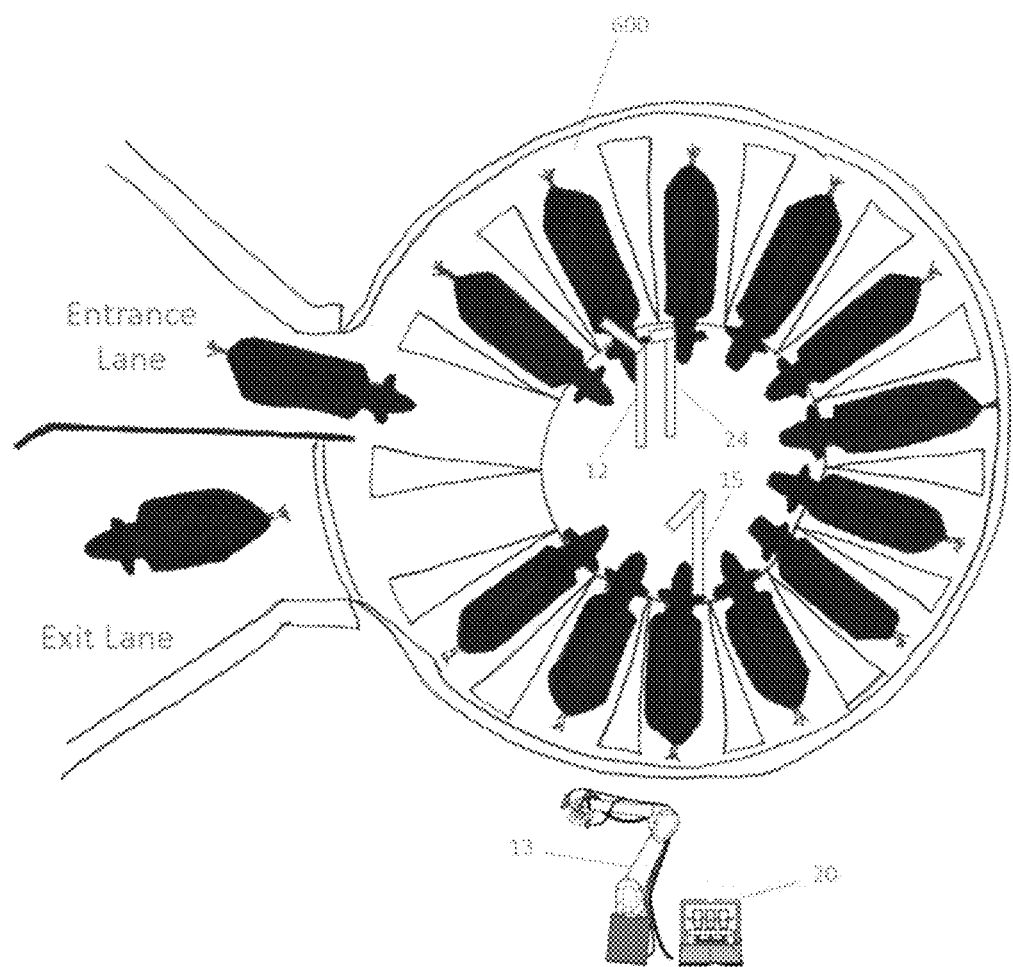
FIG. 6 depicts a series of bovines entering a rotary-style milking parlor. As the figure depicts, bovines enter the parlor through one side and place themselves within a milking stall that's rotated in a circular fashion.

FIG. 6 depicts a series of bovines entering a rotary-style milking parlor 600. As the figure depicts, bovines enter the parlor 600 through the entrance lane and place themselves within a milking stall that's rotated in a circular fashion. As the bovine enters the rotary-style milking parlor 600, it will pass the first RFID reader 12 and will shortly be followed by passing a camera ID reader 24. The first RFID reader 12 shall first identify whether or not the bovine needs an injection. After the bovine is scanned for validity by the first RFID 12 it will then be monitored and scanned by the camera ID reader 24. The camera ID reader's 24 main responsibility is to identify which cow will be receiving an injection and will act as a form of doublecheck for the dairy management computer program 17. As bovines move around together on the circular, raised, platform of the rotary-style parlor 600, the cooling unit 20 will derive liquid medication from its storage and will deploy the liquid materials into the injection mechanism. Once the second RFID 15 validates whether the bovine needs a vaccine or reproductive product, the robotic arm 13 would then position itself along with the injection mechanism to deliver the injection of the respective bovine. Once bovines reach one full rotation, the bovines shall step off the platform 600 and continue down the exit lane back to the corrals.

Figure 7:
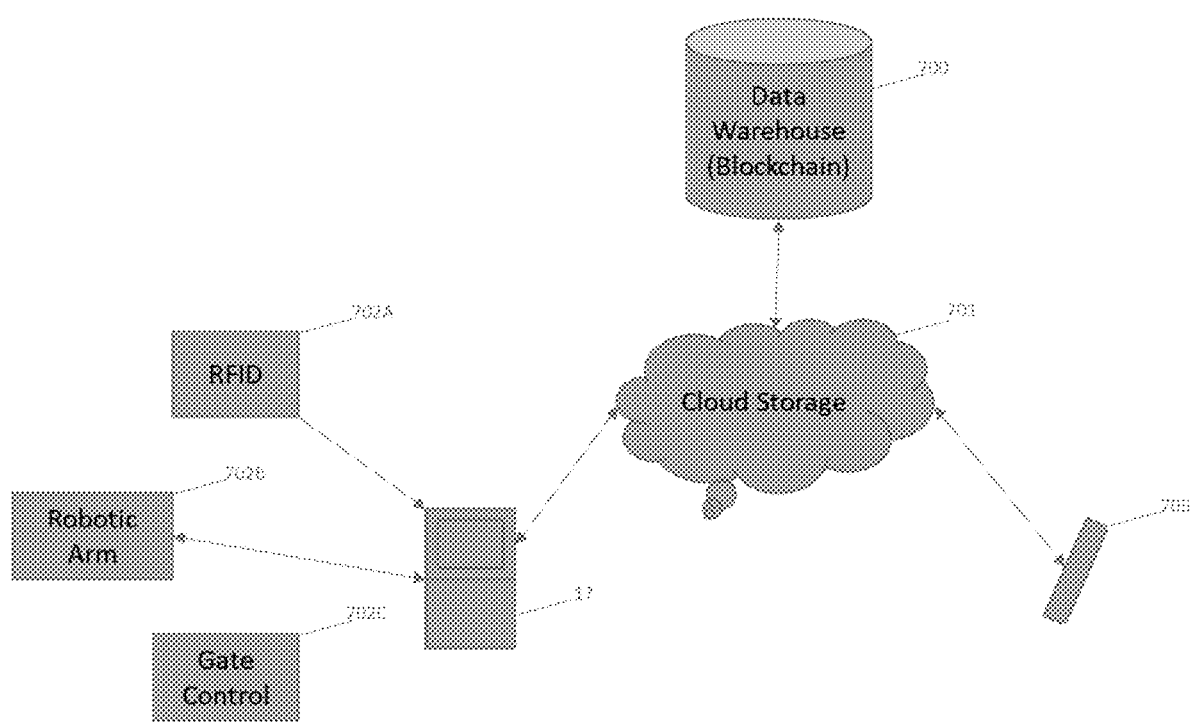
FIG. 7 is a system design of the data management process between the dairy management system, cloud-based storage, and blockchain technology.

FIG. 7 demonstrates how data is stored throughout the system and how various actions take place. Data is ultimately stored in the data warehouse 700 equipped with blockchain technologies. These blockchain technologies are primarily useful in creating a permeant ledger of the complete history of vaccines and reproductive products that were delivered to bovines on any given operation. The data that's sent to the data warehouse 700 is derived from the cloud-based storage system 701 whose primary function is to save the data collected within the dairy management computer program 17. In addition to being the initial data collector, the primary function of the dairy management computer program 17 is to interact with the RFIDs 702A and automate the gates 702C when a bovine requires an injection, interact with the robotic arm 702B to position itself to deliver injections when appropriate, and send alerts via app on a mobile device 703 to the acting dairy manager when something goes wrong within the system.

Figure 8:
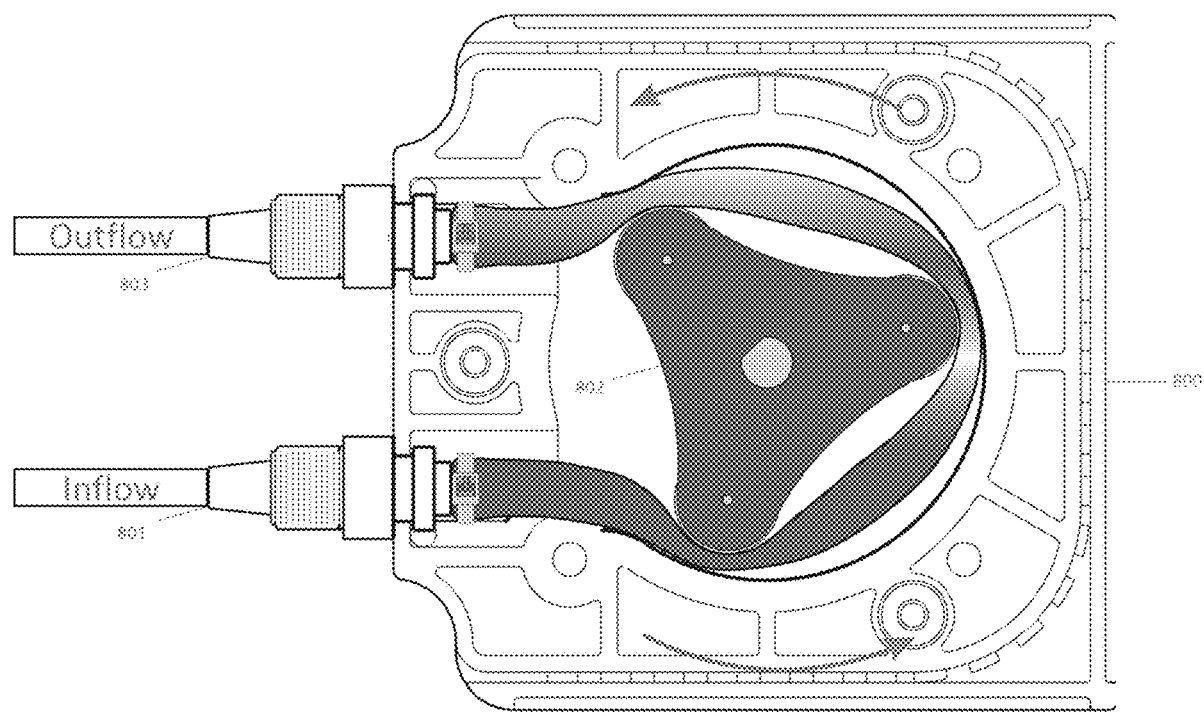
FIG. 8 demonstrates an optional add-on of how the flow of liquid material travels through a peristaltic pump rather than a traditional plunger before an injection is delivered to a bovine.

FIG. 8 demonstrates an optional add-on of how the flow of liquid material travels through a peristaltic pump 800 rather than a traditional plunger before an injection is delivered to a bovine. Liquid material is derived from the cooling-unit 20 placed near the robotic injection system 13. As the flow of liquid material travels through elongated, refrigerated, tubes 22 leading to the robotic arm 13, the liquid material then approaches the injection mechanism where it will first pass the inflow 801 portion of the peristaltic pump 800 and will be quantified respectively by a gauge 802 within the peristaltic pump 800 determining the correct dosage and flow it will allow at any point in time. For instance, if a bovine requires a 4.6 cc dose of reproductive product, then the peristaltic pump 800 will be able to adjust accordingly and make accurate measurements of the flowing liquid material, only allowing for optimal amounts of liquid material to pass on to the outflow 803 portion of the peristaltic pump 800, entering the injection mechanism and reservoir. The liquid material is then led to the respective needle 105 within the injection mechanism where an injection will be delivered. This process shall repeat for each individual bovine receiving a vaccine or reproductive product.

Figure 9:
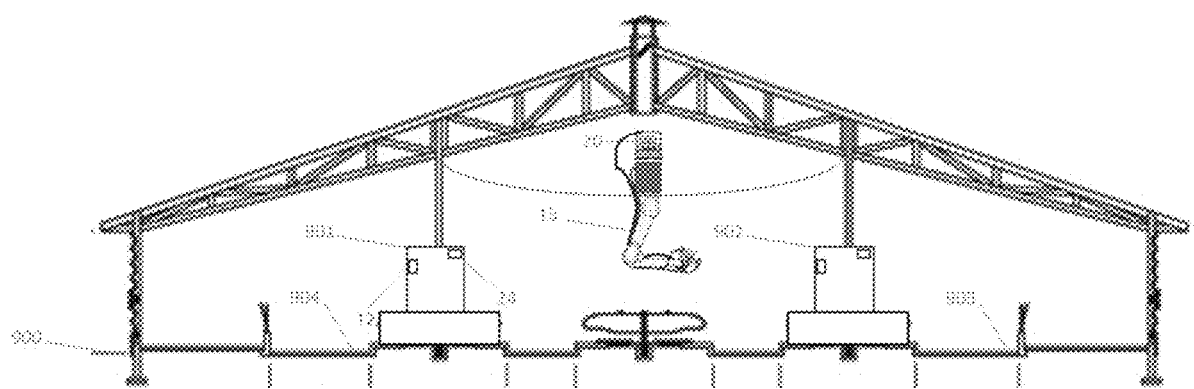
FIG. 9 depicts the optional function of utilizing the robotic injection system within a free stall, robotic-milking dairy.

FIG. 9 depicts the optional function of utilizing the robotic injection system 13 within a free stall, robotic-milking dairy 900. As bovines receive milkings from the robotic milkers 901, 902 on a daily basis, an RFID 12 and camera ID reader 24 shall be placed within the robotic milking stalls 901, 902. As the bovine enters the robotic milking stalls 901, 902, it will be scanned by the RFID 12 on the unit 901 and will be monitored and scanned by the camera ID reader 24 as well. The RFID 12 will scan the bovine to see if see requires an injection. The camera ID reader 24 will then monitor and scan the bovine to validate that the correct bovine will be receiving the correct injection based off of the identification numbers on the bovine's ear tag. Once the camera ID reader 24 validates this information, the RFID 12 will scan for medical history to see what type of injection is required. Upon selection, the robotic arm 13 shall swing along a zipline with an attached rail system and will position itself and the injection mechanism to deliver an injection to the bovine within the respective robotic milking stall 901. Upon liquid traveling from the cooling-unit 20 to the robotic arm, the injection will then be delivered. This process shall repeat for all bovines entering the robotic milking stalls 901, 902. It is also optional to have the robotic injection system near the exit lanes 903, 904 of either side of the barn. This would be a similar setup to FIG. 1. For the purpose of this specific demonstration, there will not be automated gates used and the robotic injection system shall not be on the floor of the barn.

FIG. 10 shows a detailed demonstration of how an optional rail system 1000 may be utilized to service multiple lanes for larger operations. As bovines pass through the exit lanes leading back to their respective corrals, they will be scanned by the first RFID 12 on each individual lane. The passing bovines will simultaneously be monitored and scanned by a camera ID reader 24. This is a similar process as FIG. 1 and FIG. 3. The first RFID 12 will scan the bovine to see if see requires an injection. The camera ID reader 24 will then monitor and scan the bovine to validate that the correct bovine will be receiving the correct injection based off the identification numbers on the bovine's ear tag. Following this process, the automated gates located within each exit lane will either stay open or will be activated to close depending on respective bovines either requiring injections or not requiring injections. Assuming a bovine requires an injection, the automated gate will close and the robotic arm 13 attached to the rail system 1000 shall glide over to the respective lane and position itself to deliver the injection to the bovine. The second RFID 15 scans bovines within the injection site for their medical history and conception statistics. With the cooling-unit 20 placed directly on top of the robotic arm 13, this allows for feasible flow of liquid materials derived from the cooling-unit 20 and ending in the injection mechanism. Once the robotic arm 13 positions itself along with the injection mechanism to deliver the injection, the robotic arm 13 will then glide over to the next exit lane where a bovine requires an injection. This transportation is possible by allowing the robotic arm 13 to be attached upside down on a rail-system 1000. This rail-system 1000 may also include support beams on each side of the unit to maintain balance while injections are being delivered by the robotic arm 13, as seen in the figure.

What is claimed is:

1. A system for delivering one or more injections containing pharmaceutical agents in an autonomous manner to a bovine the system comprising of:
   an enclosed cooling unit containing a plurality of containers that are maintained at a certain temperature with each container accommodating a single pharmaceutical agent;
   a robot comprising:
      an arm having a proximal and distal end and composed of one or more segments;
      a head at the distal end of said arm the head further comprising:
         a plurality of syringes;
         an infrared camera;
         a laser rangefinder; and
         a camera;
   a plurality of tubes to allow said cooling unit and said syringes to be in fluid communications with each other;
   a computer that executes a dairy management software that is networked with and controls said cooling unit and said robot; and
   a means of identifying the bovine and transmitting such information to said computer;
   wherein said robot is able to make a subcutaneous or intramuscular injection into a bovine using any pharmaceutical agent contained within said cooling unit through one or more said syringes.

2. The system of claim 1 wherein said pharmaceutical agents comprise the set of vaccines, reproductive hormones, and veterinary prescribed medications.

3. The system of claim 1 additionally comprising a plurality of lanes leading the bovines to said robot the lanes having:
   a first gate with two means of electronically identifying the bovine approaching first gate;
   a second gate with a single mean of electronically identifying the bovine approaching second gate;
   the distance between first and second gate sufficient to accommodate a single bovine; and
   said robot positioned between first and second gate.

4. The system of claim 3 wherein said two means of electronically identifying a bovine are a radio frequency identifier and a camera identifier.

5. The system of claim 3 wherein said one mean of electronically identifying a bovine is a radio frequency identifier.

6. The system of claim 3 wherein said lane between first and second gate may further comprise bumpers to further constrain the bovine undergoing an injection.

7. The system of claim 3 wherein said robot and cooling unit is suspended above said plurality of lanes by a rail and is capable of being positioned proximate to a bovine in any one of the lanes.

8. The system of claim 1 wherein said head is able to discard needles unwanted needles to be replaced by a new needle at a certain frequency.

9. The system of claim 1 wherein said head further comprises a camera to determine if a needle is damaged or otherwise unusable.

10. The system of claim 1 wherein said dairy management software may communicate with cellular networks to send text messages containing alarms to previously identified individuals.

11. The system of claim 1 further comprising:
one or more robotic milking stalls having a radio frequency identifier and a camera identifier to identify the bovine currently stalled by the robotic milking stall; and
a rail system above the bovine enclosure containing the robotic milking stalls capable of transporting said robot and cooling unit to the bovine held by the robotic milking stall.

12. The system of claim 1 wherein said means of identifying the bovine is a QR code or bar code present outside of the bovine or a radio frequency identifier found within the bovine.

13. The system of claim 1 wherein said head contains a spray paint, teat dipping, or sanitation spray device.

14. The system of claim 1 wherein said cooling unit is capable of registering a new container containing a pharmaceutical agent by reading a QR or bar code label on the container.

15. The system of claim 1 wherein said dairy management software is managed on a remote server and is accessible via a network.

* * * * *